(12) United States Patent
Kim

(10) Patent No.: US 10,973,493 B2
(45) Date of Patent: Apr. 13, 2021

(54) ULTRASOUND DIAGNOSTIC APPARATUS, HOLDER ASSEMBLY, AND METHOD FOR CONTROLLING THE ULTRASOUND DIAGNOSTIC APPARATUS

(71) Applicant: SAMSUNG MEDISON CO., LTD., Gangwon-do (KR)

(72) Inventor: Chil Su Kim, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 693 days.

(21) Appl. No.: 15/094,409

(22) Filed: Apr. 8, 2016

(65) Prior Publication Data

US 2017/0150944 A1     Jun. 1, 2017

(30) Foreign Application Priority Data

Dec. 1, 2015 (KR) .................. 10-2015-0169725

(51) Int. Cl.
*A61B 8/00*          (2006.01)

(52) U.S. Cl.
CPC .............. *A61B 8/4444* (2013.01); *A61B 8/00* (2013.01); *A61B 8/4433* (2013.01); *A61B 8/4438* (2013.01); *A61B 8/4477* (2013.01); *A61B 8/54* (2013.01); *A61B 8/56* (2013.01); *A61B 8/4405* (2013.01); *A61B 8/4427* (2013.01); *A61B 8/4472* (2013.01)

(58) Field of Classification Search
CPC ... A61B 8/4405; A61B 8/4433; A61B 8/4438; A61B 8/4477; A61B 8/54
See application file for complete search history.

(56) References Cited

U.S. PATENT DOCUMENTS

| 5,505,203 A | * | 4/1996 | Deitrich | ................... A61B 8/00 600/437 |
| 5,615,678 A | * | 4/1997 | Kirkham | .............. G10K 11/004 600/459 |
| 7,566,305 B2 | * | 7/2009 | Onodera | .................. A61B 8/14 439/449 |

(Continued)

FOREIGN PATENT DOCUMENTS

| CN | 103027710 A | 4/2013 |
| CN | 104414682 A | 3/2015 |

(Continued)

OTHER PUBLICATIONS

Extended European Search Report dated Apr. 5, 2017 issued in European Patent Application No. 16184010.3.

(Continued)

*Primary Examiner* — Katherine L Fernandez
*Assistant Examiner* — Colin T. Sakamoto
(74) *Attorney, Agent, or Firm* — Morgan, Lewis & Bockius LLP

(57) ABSTRACT

Disclosed is an ultrasound diagnostic apparatus. The ultrasound diagnostic apparatus includes a holder implemented to hold a probe; an object sensor for detecting physical changes around the holder; an electromagnetic wave sensor for detecting electromagnetic waves around the holder; and a controller for determining a port name for a probe held in the holder, based on sensing values from the object sensor and electromagnetic wave sensor.

15 Claims, 14 Drawing Sheets

(56) References Cited

U.S. PATENT DOCUMENTS

| | | | |
|---|---|---|---|
| 7,772,802 B2* | 8/2010 | Manico | H02J 50/10 320/108 |
| 8,033,174 B2* | 10/2011 | Shin | A61B 8/00 73/661 |
| 2004/0179332 A1* | 9/2004 | Smith | G01S 7/52082 361/679.41 |
| 2006/0036177 A1* | 2/2006 | Onodera | A61B 8/14 600/459 |
| 2006/0173346 A1* | 8/2006 | Lee | A61B 8/4438 600/459 |
| 2007/0293763 A1* | 12/2007 | Matsumura | A61B 8/12 600/459 |
| 2009/0069690 A1* | 3/2009 | Shin | A61B 8/4405 600/459 |
| 2010/0191121 A1* | 7/2010 | Satoh | A61B 8/56 600/459 |
| 2011/0148364 A1* | 6/2011 | Ota | B25J 5/007 320/162 |
| 2012/0291809 A1* | 11/2012 | Kuhe | A47L 5/24 134/18 |
| 2013/0083629 A1 | 4/2013 | Ji et al. | |
| 2014/0107487 A1* | 4/2014 | Kim | A61B 8/4444 600/459 |
| 2015/0045673 A1* | 2/2015 | Kim | A61B 8/5207 600/459 |
| 2015/0265253 A1* | 9/2015 | Kim | A61B 8/4281 600/443 |
| 2016/0106396 A1* | 4/2016 | Jin | A61B 8/4477 600/437 |

FOREIGN PATENT DOCUMENTS

| | | |
|---|---|---|
| CN | 104434206 A | 3/2015 |
| JP | H10-108864 A | 4/1998 |
| JP | 2000-107176 A | 4/2000 |
| JP | 2008-253500 A | 10/2008 |
| KR | 10-2011-0094281 A | 8/2011 |
| KR | 10-2015-0108694 A | 9/2015 |

OTHER PUBLICATIONS

Chinese Office Action dated Jul. 24, 2020 issued in Chinese Patent Application No. 201610552046.3 (with English translation).

* cited by examiner (a)

(b)

(c)

ULTRASOUND DIAGNOSTIC APPARATUS, HOLDER ASSEMBLY, AND METHOD FOR CONTROLLING THE ULTRASOUND DIAGNOSTIC APPARATUS

CROSS-REFERENCE TO RELATED APPLICATION(S)

This application claims the benefit under 35 U.S.C. § 119(a) of a Korean patent application filed on Dec. 1, 2015 in the Korean Intellectual Property Office and assigned Serial No. 10-2015-0169725, the entire disclosure of which is incorporated hereby incorporated by reference.

BACKGROUND

1. Field

The present disclosure relates to an ultrasound diagnostic apparatus, holder assembly, and method for controlling the ultrasound diagnostic apparatus.

2. Description of the Related Art

An ultrasound diagnostic apparatus is a device for transmitting ultrasound from the surface of a subject toward a target point of the inside of the subject, and obtaining tomograms of soft tissue or images about blood flows in an invasive way by receiving reflected echo ultrasound.

The ultrasound diagnostic apparatus is widely used because it is compact and inexpensive, and is able to display diagnostic images in real time, as compared with X-ray devices, Computerized Tomography (CT) scanners, Magnetic Resonance Imaging (MRI) devices, etc.

The ultrasound diagnostic apparatus includes a probe for transmitting ultrasound to a subject and receiving echo ultrasound reflected from the subject to obtain an ultrasound image of the subject.

There may be multiple probes equipped in the ultrasound diagnostic apparatus, and each probe may be coupled with a port of the ultrasound diagnostic apparatus over a wireless communication network or via a cable. Each probe may be held in a holder equipped in the ultrasound diagnostic apparatus.

Typically, if the user selects one of the plurality of probes held in a holder, the user has to manually type in which port the selected probe corresponds to. For example, in a case that there are first and second holders equipped in the ultrasound diagnostic apparatus and that the user selects a probe held in the second holder, the user has to type in whether the probe held in the second holder is coupled with a first port or a second port directly to the ultrasound diagnostic apparatus.

SUMMARY

The present disclosure provides an ultrasound diagnostic apparatus and method for controlling the same, by which to automatically determine a port coupled with each probe no matter which one of a plurality of holders the probe is held in.

The present disclosure also provides an ultrasound diagnostic apparatus and method for controlling the same, by which a port coupled with each probe is appropriately determined.

The present disclosure also provides a holder assembly to create a sensing value required for an ultrasound diagnostic apparatus to automatically determine a port coupled with each probe.

In accordance with an aspect of the present disclosure, an ultrasound diagnostic apparatus is provided. The ultrasound diagnostic apparatus includes a holder implemented to hold a probe; an object sensor for detecting physical changes around the holder; an electromagnetic wave sensor for detecting electromagnetic waves around the holder; and a controller for determining a port name for a probe held in the holder, based on sensing values from the object sensor and electromagnetic wave sensor.

The object sensor may include a conductor sensor arranged on or around the holder, and the conductor sensor may detect a change in impedance or resonance frequency.

The object sensor may include a photo interrupter arranged on or around the holder, and the photo interrupter may include a light source for irradiating light into the holder and a light receiver for receiving the light.

The object sensor may include a magnetic sensor.

The object sensor may include a capacitance sensor, and the capacitance sensor may detect a change in impedance or resonance frequency.

The electromagnetic wave sensor may include an Electro-Magnetic Interference (EMI) sensor.

The controller may map the port name and a holder name of the holder.

The ultrasound diagnostic apparatus may further include a sensing value processor for determining whether a probe is held in or out of a holder, based on a sensing value from the object sensor.

The controller may determine a port name mapped to a holder name of a holder of which a probe is held out, and activate a probe that corresponds to the mapped port name.

The ultrasound diagnostic apparatus may further include a display unit, wherein the controller may determine a port name mapped to a holder name of a holder of which a probe is held out, and wherein the display unit may display the holder name and the mapped port name.

The same number of the object sensors and electromagnetic wave sensors as the number of the holders may be arranged.

If the sensing value processor determines that a probe is held in a first holder based on a sensing value from the object sensor, the controller may update a mapping table based on a sensing value from the electromagnetic wave sensor.

The controller may stop operation of a probe when the probe is held in a holder.

In accordance with another aspect of the present disclosure, a holder assembly is provided. The holder assembly includes a holder implemented to hold a probe; an object sensor for detecting physical changes around the holder; an electromagnetic wave sensor for detecting electromagnetic waves around the holder; and a sensing value processor for determining whether a probe is held in or held out, based on sensing values from the object sensor and electromagnetic wave sensor.

The holder assembly may further include a communication unit for sending a result of determination of the controller to a main body.

The object sensor may include a conductor sensor arranged on or around the holder, and the conductor sensor may detect a change in impedance or resonance frequency.

The object sensor may include a photo interrupter arranged on or around the holder, and the photo interrupter may include a light source for irradiating light into the holder and a light receiver for receiving the light.

The object sensor may include a magnetic sensor.

In accordance with another aspect of the present disclosure, a method for controlling an ultrasound diagnostic apparatus is provided. The methods includes detecting physical changes around a holder; detecting electromagnetic waves around the holder; and determining a port name for a probe held in the holder, based on the physical change and the electromagnetic wave.

Detecting physical changes around a holder may include determining whether the probe is held in or held out.

The method may further include activating the probe corresponding to the holder based on an existing stored mapping table, if it is determined that the probe is held out of the holder.

Other aspects, advantages, and salient features of the disclosure will become apparent to those skilled in the art from the following detailed description, which, taken in conjunction with the annexed drawings, discloses exemplary embodiments of the disclosure.

BRIEF DESCRIPTION OF THE DRAWINGS

The above and other features and advantages of the present disclosure will become more apparent by describing in detail exemplary embodiments thereof with reference to the attached drawings in which.

Throughout the drawings, like reference numerals will be understood to refer to like parts, components, and structures.

DETAILED DESCRIPTION

Figure 1:
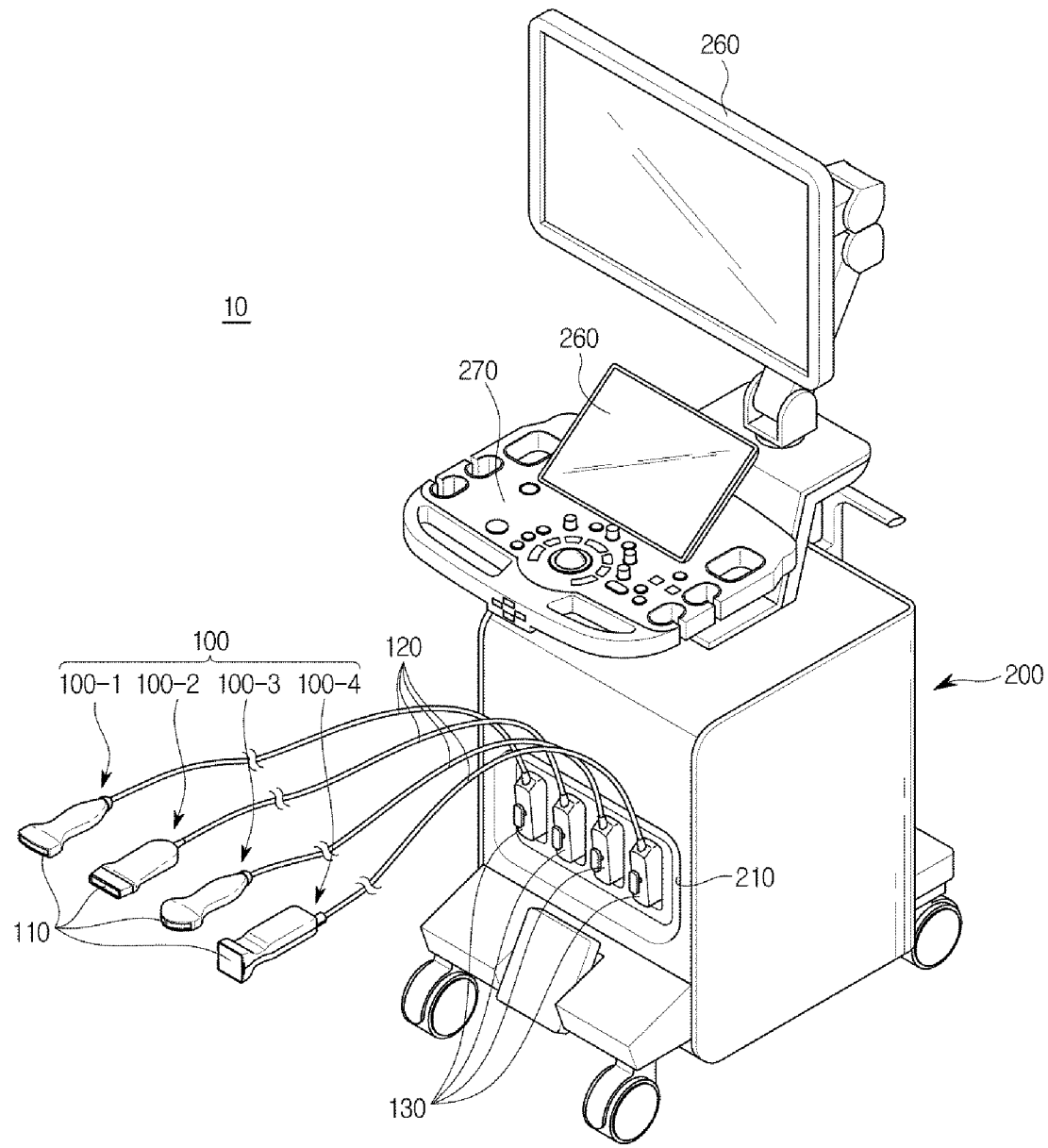
FIG. 1 is an exterior view of an ultrasound diagnostic apparatus, according to an embodiment of the present disclosure.

The present disclosure will now be described more fully with reference to the accompanying drawings, in which exemplary embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Like reference numerals in the drawings denote like elements, and thus their description will be omitted. In the description of the present disclosure, if it is determined that a detailed description of commonly-used technologies or structures related to the embodiments of the present disclosure may unnecessarily obscure the subject matter of the invention, the detailed description will be omitted. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

Embodiments of an ultrasound diagnostic apparatus and method for controlling the same will be described in detail with reference to accompanying drawings.

Figure 2:
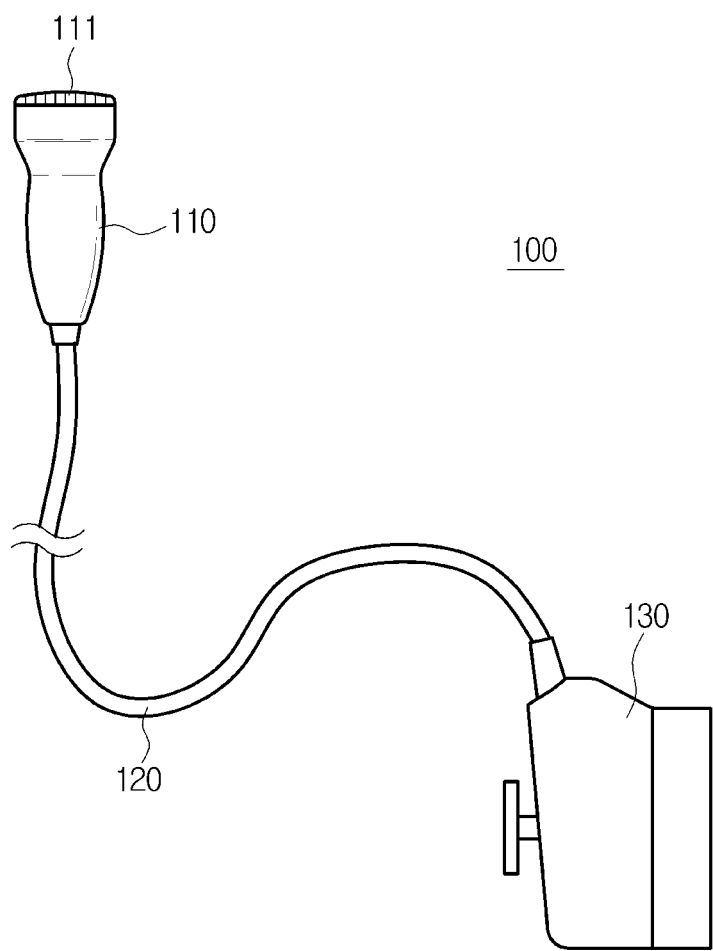
FIG. 2 is an exterior view of a probe.
Figure 3:
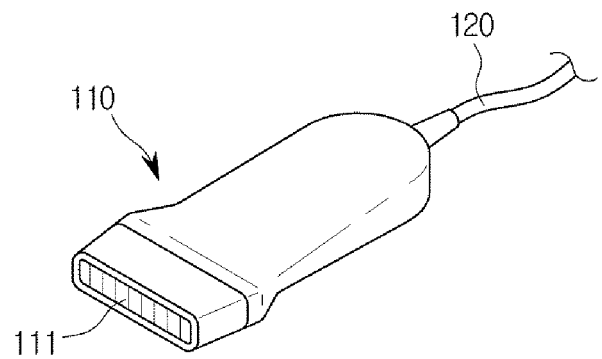
FIG. 3 shows various probes in different shapes.
Figure 3:
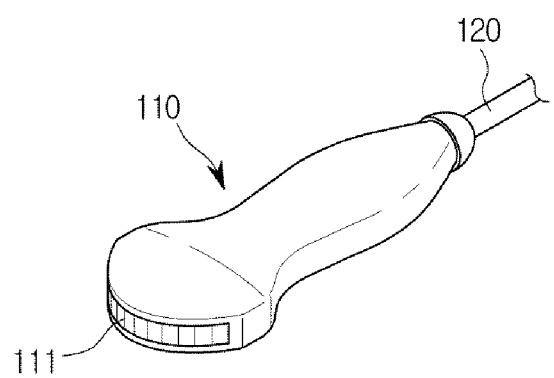
Figure 3:
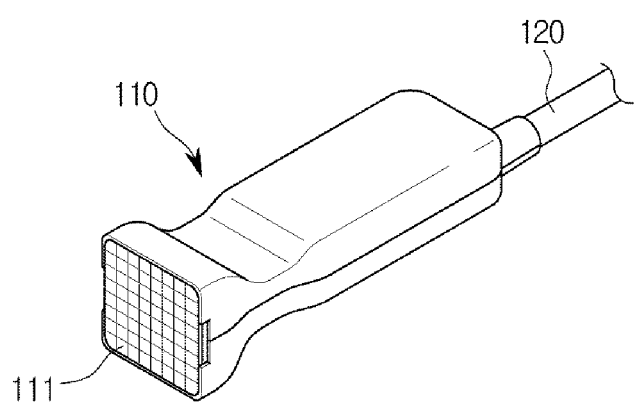
Figure 4:
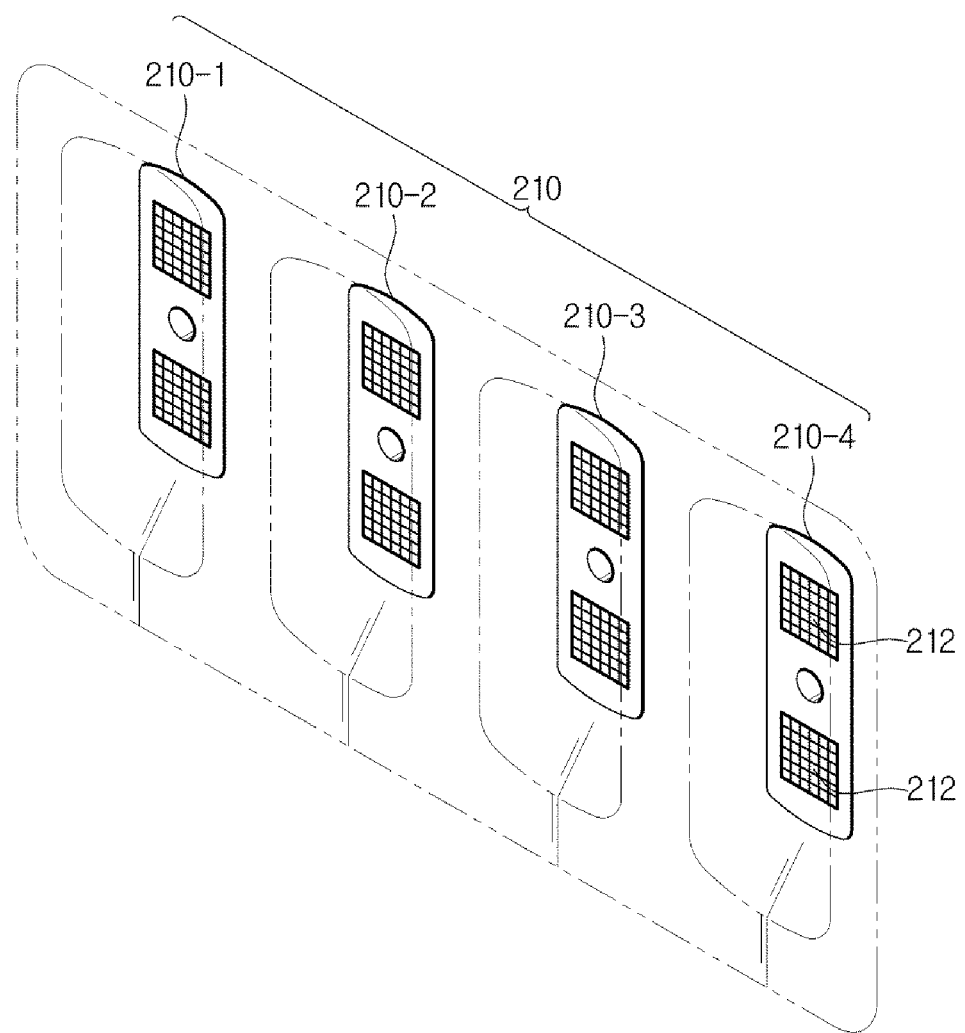
FIG. 4 is an enlarged view of a plurality of ports equipped in a main body.
Figure 5:
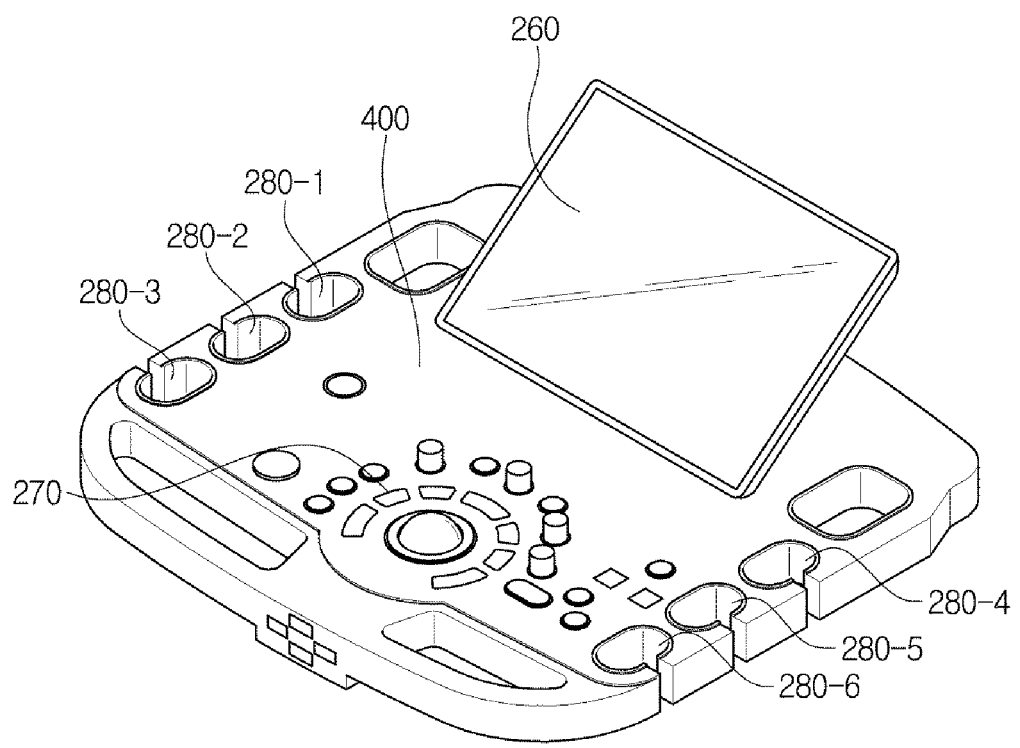
FIG. 5 is an enlarged view of a plurality of holders equipped in a main body.

FIG. 1 is an exterior view of an ultrasound diagnostic apparatus, according to an embodiment of the present disclosure, FIG. 2 is an exterior view of a probe, FIG. 3 shows various probes in different shapes, FIG. 4 is an enlarged view of a plurality of ports equipped in a main body, and FIG. 5 is an enlarged view of a plurality of holders equipped in a main body.

Referring to FIG. 1, an ultrasound diagnostic apparatus 10 may include a probe 100 and a main body 200. The probe 100 shown in FIG. 2 may be one of a plurality of probes 100-1 to 100-4 shown in FIG. 1.

The probe 100 may transmit ultrasound to a subject, and receive and convert echo ultrasound reflected from the subject to an electric signal (hereinafter, referred to as an ultrasound signal).

The main body 200 may be coupled with the plurality of probes 100-1 to 100-4 through at least one port 210. The plurality of probes 100-1 to 100-4 that may be coupled with the main body 200 may include first to fourth probes 100-1, 100-2, 100-3, and 100-4.

The main body 200 may create an ultrasound image based on the ultrasound signal received from one of the first to fourth probes 100-1 to 100-4.

The main body 200 may be a workstation having a display unit 260 and an input unit 270, and may be coupled with the first to fourth probes 100-1 to 100-4.

There may be a plurality of display units 260 and input units 270 equipped in the main body 200.

Features and operation methods of the first to fourth probes 100-1 to 100-4 will be described in detail in connection with FIG. 2. For convenience of explanation, the probe 100 refers to each of the first to fourth probes 100-1 to 100-4, and may be one of the first to fourth probes 100-1 to 100-4.

The probe 100 may include a transducer 110 for transmitting/receiving ultrasound, a probe connector 130 for transmitting/receiving signals to/from the main body 200, and a cable 120 connecting the transducer 110 and the probe connector 130.

The transducer 110 may transmit/receive ultrasound to/from a subject to obtain an ultrasound image of the inside of the subject.

Specifically, the transducer 110 may include a transducer module 111 for converting between electric signals and vibration (or acoustic) energy, which may use vibrators, such as piezoelectrics (not shown) to transmit ultrasound to the subject and receive echo ultrasound reflected from the subject.

If the number of the vibrators is 64 to 256, coupling elements as many as the number of the vibrators are required in coupling the probe 100 and the main body 200.

The object may be, but not exclusively, a living body of a human or animal, an organ in the living body, such as blood vessels, bones, muscles, etc., or anything whose internal structure may be imaged by the ultrasound diagnostic apparatus 10.

Referring to FIG. 3, the transducer 110 may be implemented as a linear transducer having the linear surface as shown in (a) of FIG. 3, as a convex transducer having the convex and curved surface as shown in (b) of FIG. 3, or as a matrix transducer as shown in (c) of FIG. 3, depending on an arrangement form of the transducer module 111. However, the transducer 110 is not limited thereto, and may be implemented in any other form than those shown in FIG. 3, which is known to an ordinary skill in the art, such as a phased array transducer.

The transducer 110 is connected to an end of the cable 120, the other end of which may be connected to the probe connector 130.

The probe connector 130 is connected to a port of the main body 200 for transmitting/receiving electric signals with the main body 200.

The probe connector 130 may be implemented as a connector combined with a port of the main body 200 implemented as a female connector.

Referring to FIG. 4, there may be a plurality of ports 210; 210-1 to 210-4 formed on the main body 200, and each port 210 may include a socket 212 to be coupled with pins of the probe connector 130 of the probe 100.

The plurality of ports 210-1 to 210-4 equipped in the main body 200 may include first to fourth ports 210-1 to 210-4. A probe 100 coupled with the first port 210-1 is called the first probe 100-1; a probe 100 coupled with the second port 210-2 is called the second probe 100-2; a probe 100 coupled with the third port 210-3 is called the third probe 100-3; a probe 100 coupled with the fourth port 210-4 is called the fourth probe 100-4.

An ultrasound signal generated by each probe 100 may be transmitted to the main body 200 through the port 210 coupled with each probe 100.

Furthermore, referring to FIG. 5, at least one holder 280 may be arranged in the main body 200 to hold the probe 100. There may be a plurality of holders 280 arranged independently of the number of the probes 100 or the number of the ports 210.

Assume herein that first to sixth holders 280-1 to 280-6 are arranged in the body 200.

The first to sixth holders 280-1 to 280-6 may be located around the display unit 260 or input unit 270 of the main body 200, as shown in FIG. 5, but their locations are not limited thereto.

Figure 6:
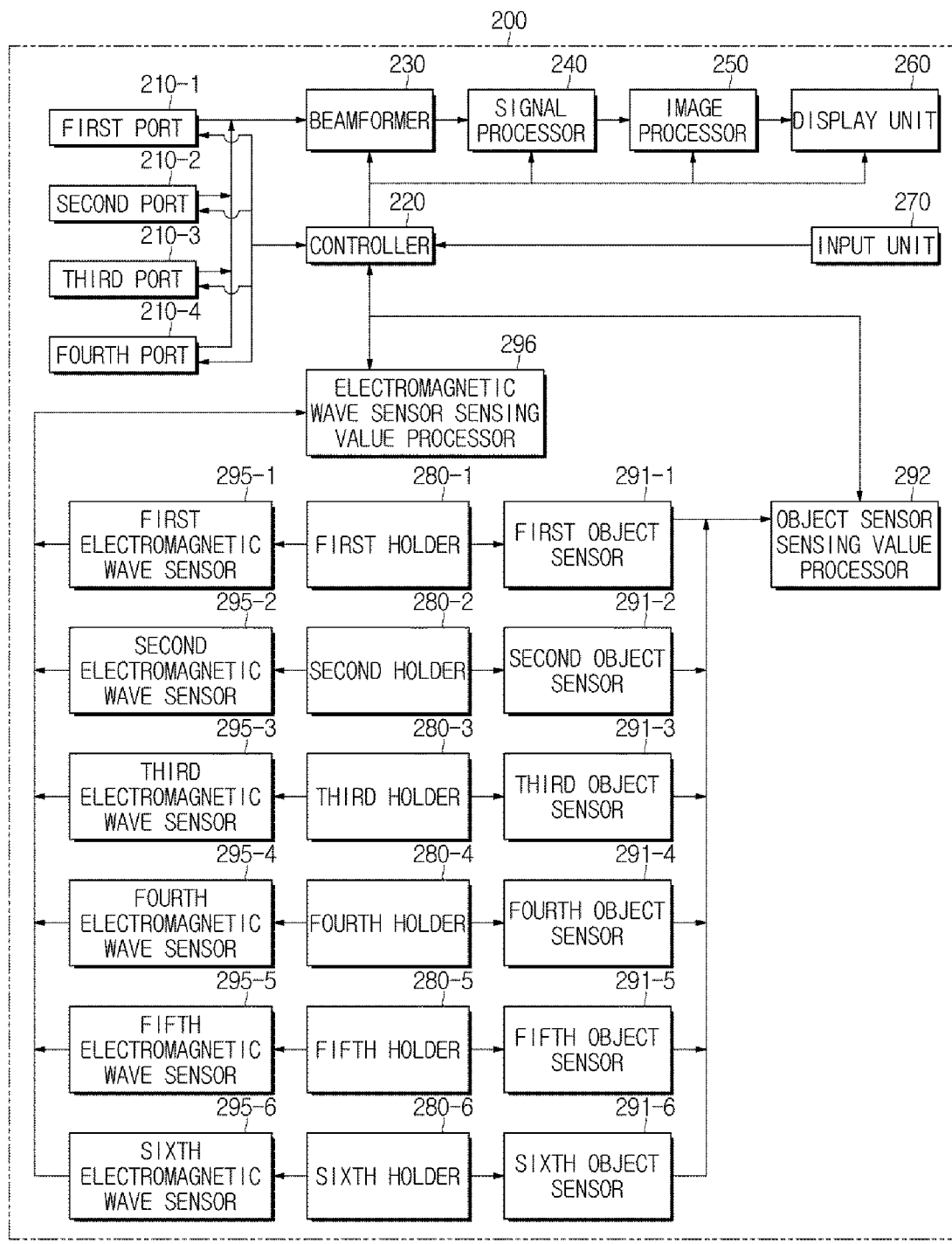
FIG. 6 is a control block diagram of a main body, according to an embodiment of the present disclosure.

The main body 200 will be described in more detail in connection with FIGS. 6, 7A, 7B, and 7C. FIG. 6 is a control block diagram of a main body, according to an embodiment of the present disclosure.

Referring to FIG. 6, the main body 200 may include first to fourth ports 210-1 to 210-4, a controller 220, a beamformer 230, a signal processor 240, an image processor 250, a display unit 260, an input unit 270, first to sixth holders 280-1 to 280-6, first to sixth object sensors 291-1 to 291-6, an object sensor sensing value processor 292, first to sixth electromagnetic wave sensors 295-1 to 295-6, and an electromagnetic wave sensor sensing value processor 296.

Although FIG. 6 shows that the main body 200 includes four ports 210-1 to 210-4 and six holders 280-1 to 280-6, the number of ports 210 and holders 280 is not limited thereto.

Upon reception of an ultrasound signal from the probe 100 connected to at least one or more ports among the first to fourth ports 210-1 to 210-4, the at least one or more ports may forward the ultrasound signal to the beamformer 230.

The first to fourth ports 210-1 to 210-4 may include sockets 212 to be electrically coupled with the probe 100.

The controller 220 may generate control signals to control the respective elements of the probe 100 and main body 200.

For example, the controller 220 may generate control signals to operate the probe 100, or generate control signals to control the beamformer 230, the signal processor 240, the image processor 250, and the display unit 260 based on ultrasound signals received from the probe 100, and process various information obtained by the probe 100 according to a stored program.

Furthermore, in an embodiment, the controller 220 may map each of the first to fourth ports 210-1 to 210-4 to one of the first to sixth holders 291-1 to 291-6 based on information received from the electromagnetic wave sensor sensing value processor 296 and the object sensor sensing value processor 292. A plurality of port names, e.g., port numbers, and holder names, e.g., holder numbers corresponding to the port names may be stored in a mapping table. An operation procedure of the controller 220 will be described later in detail.

The controller 220 may include a memory for storing a program and data, e.g., mapping table, to control the respective elements of the probe 100 and main body 200, and a processor for controlling the probe 100 and main body 200 according to the program and data stored in the memory.

The beamformer 230 is a device to give a proper time delay to ultrasound for transmission or received echo ultrasound, in order for the ultrasound produced by the transducer of the probe 100 to be focused on a target point of the subject at a desired moment of time, or for the echo ultrasound bounced off the target point of the subject to overcome a time difference in arriving the transducer.

In the ultrasound diagnostic apparatus 10, the beamformer 230 may be included in the main body 200 that corresponds to a back-end as shown in FIG. 6, or may be included in the probe 100 that corresponds to a front-end. Embodiments of the beamformer 230 are not limited thereto, and all or parts of elements of the beamformer 230 may be included in some parts of the front-end and back-end. However, for convenience of explanation, it is assumed that the beamformer 230 is included in the main body 200.

The signal processor 240 may convert a signal received from the beamformer 230 into a format suitable for image processing. For example, the signal processor 240 may perform filtering to eliminate noise outside a desired frequency band.

Furthermore, the signal processor 240 may be implemented by a digital signal processor (DSP), and may generate ultrasound image data by performing envelope detection to detect the amplitude of the echo ultrasound based on the signal received from the beamformer 230.

The image processor 250 may generate an image for the user, e.g., a doctor or patient, to visually check the inside of a subject, e.g., a human body, based on the ultrasound image data generated by the signal processor 240.

The image processor 250 may send the display unit 260 an ultrasound image generated using the ultrasound image data.

In addition, the image processor 250 may further perform extra image processing on the ultrasound image in some embodiments. For example, the image processor 250 may further perform post image processing, such as compensating for or readjusting contrast, brightness, or sharpness of the ultrasound image.

Such extra image processing of the image processor 250 may be performed according to a predetermined setting, or in response to a user instruction or command input through the input unit 270.

The display unit 260 may display the ultrasound image generated by the image processor 250, thereby enabling the user to visually examine the internal structure or tissue of the subject.

The input unit 270 may receive predetermined instructions or commands from the user for controlling the ultrasound diagnostic apparatus 10. The input unit 270 may also include a user interface, such as e.g., a keyboard, a mouse, a trackball, a touch screen, a paddle, etc.

For example, the input unit 270 may receive instructions to operate or freeze operation of any of the plurality of probes 100-1 to 100-6.

The first to sixth holders 280-1 to 280-6 may be able to hold the probe 100.

In a case the main body 200 is coupled with the first to fourth probes 100-1 to 100-4 through the first to fourth ports 210-1 to 210-4, the first to sixth holders 280-1 to 280-6 may be able to hold the first to fourth probes 100-1 to 100-4. In this case, a holder 280 may hold one probe 100.

The first to sixth holders 280-1 to 280-6 may each be equipped with an object sensor 291 and an electromagnetic wave sensor 295. In this case, there may be the same number of object sensors 291 and electromagnetic wave sensors 295 as the number of holders 280, and the object sensor 291 and electromagnetic wave sensor 295 may be located on or around the holder 280.

The object sensor 291 may detect physical changes around the holder 280. For example, the object sensor 291 may be a conductor sensor, an infrared sensor, an Light Emitting Diode (LED) sensor, or a magnetic sensor.

If the object sensor 291 is the conductor sensor, the conductor sensor may detect different impedance or a resonance frequency depending on whether the holder 280 holds the probe 100. In this regard, the object sensor sensing value processor 292 may determine whether the probe 100 is held in based on the impedance or resonance frequency, i.e., a sensing value detected by the conduct sensor.

Various embodiments of the object sensor 291 will be described later in connection with FIGS. 7A to 7C.

The object sensor sensing value processor 292 may determine which one of the first to sixth holders 210-1 to 210-6 the probe 100 is held in or held out, based on sensing values from the plurality of object sensors 291-1 to 291-6.

The electromagnetic wave sensor 295 may detect electromagnetic waves produced around the holder 280. For example, the electromagnetic wave sensor 295 may be an Electro-Magnetic Interference (EMI) sensor.

In the case the electromagnetic wave sensor 292 is the EMI sensor, the EMI sensor may detect different electromagnetic wave signals depending on whether the holder 280 holds the probe 100 and whether the probe 100 held in the holder 280 is activated. In this regard, the electromagnetic wave sensor sensing value processor 296 may determine whether the probe 100 is activated based on the electromagnetic wave signals detected by the EMI sensor.

Specifically, if the probe 100 is held in the holder 280 while being activated, the EMI sensor may detect electromagnetic waves, and otherwise if the probe 100 held in the holder 280 is not activated, the EMI sensor may not detect any electromagnetic wave.

The electromagnetic wave sensor sensing value processor 296 may determine which one of the first to sixth holders 210-1 to 210-6 the probe 100 is held in while being activated, based on sensing values from the plurality of electromagnetic wave sensors 295-1 to 295-6.

In some embodiments, the controller 220, the object sensor sensing value processor 292, and the electromagnetic wave sensor sensing value processor 296 may be implemented to have separate memories and processors or implemented with a single memory and a single processor. If the object sensor sensing value processor 292 and the electromagnetic wave sensor sensing value processor 296 are implemented with a single memory and a single processor, a single sensing value processor may perform functions of the object sensor sensing value processor 292 and the electromagnetic wave sensor sensing value processor 296.

Figure 7A:
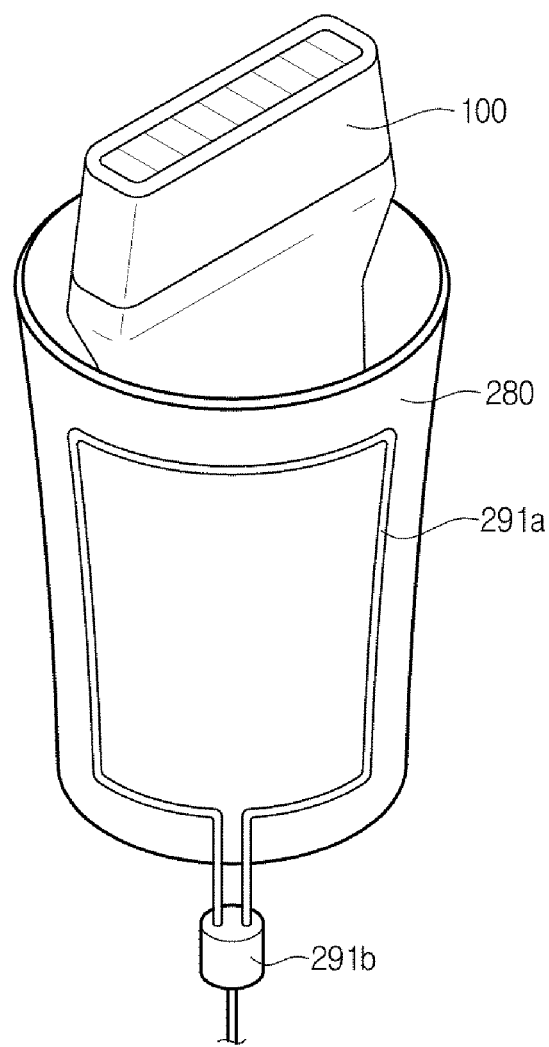
FIGS. 7A to 7C show various embodiments of an object sensor equipped in a holder.
Figure 7B:
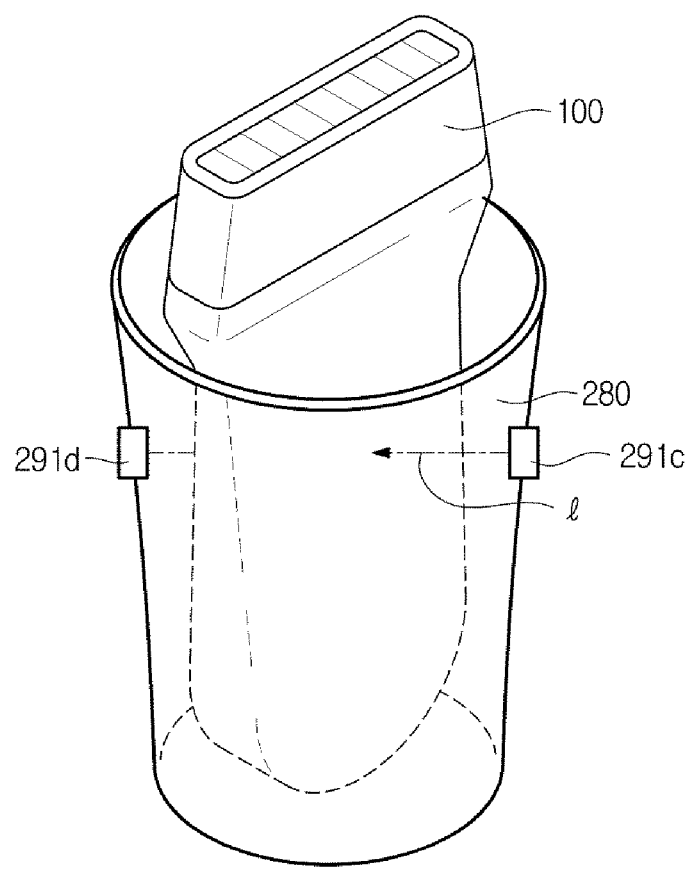
Figure 7C:
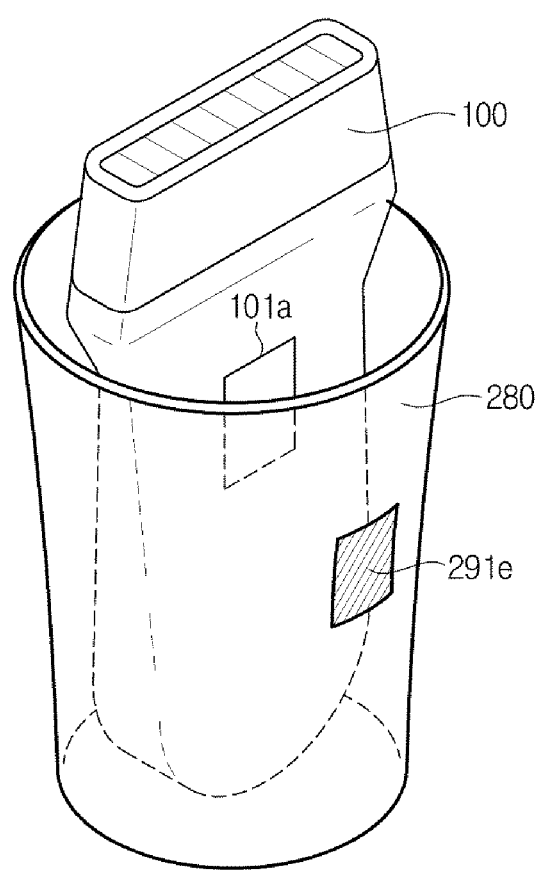

FIGS. 7A to 7C show various embodiments of an object sensor equipped in a holder.

Referring to FIG. 7A, the object sensor 291 may be implemented as a conduct sensor, which may include a wire 291a attached to the holder 280 and an impedance measurer 291b. The impedance measurer 291b may measure different impedance or resonance frequency depending on whether the probe 100 is held in or out of the holder 280, because the probe 100 may be enclosed by a copper material.

Alternatively, referring to FIG. 7B, the object sensor 291 may be implemented as a photo interrupter, which may include any sensor, such as an infrared sensor, an LED sensor, etc., that includes a light source 291c and a light receiver 291d. If the probe 100 is held in the holder 280, the probe 100 cuts off light (1) irradiated from the light source 291c, and the light receiver 291d may not detect light. Otherwise if the probe 100 is held out of the holder 280, the light (1) irradiated from the light source 291c may be detected by the light receiver 291d.

Alternatively, referring to FIG. 7C, the object sensor 291 may be implemented as a magnetic sensor 291e. The magnetic sensor 291e may determine whether the probe 100 is held in or held out of the holder 280 by detecting a magnetic substance 101a attached to the probe 100.

Besides, the object sensor 291 may be implemented as a capacitance sensor and may determine whether the probe 100 is held in or held out of the holder 280 by detecting impedance, i.e., capacitance, or resonance frequency, but is not limited thereto.

The electromagnetic wave sensor 292 may be implemented as an EMI sensor and attached onto or around the holder 280 to detect a signal, i.e., an electromagnetic wave signal based on whether the probe 100 is held in the holder 280.

The object sensor 291 and electromagnetic wave sensor 292 may be separately arranged on each holder 280, or may be arranged as a single sensor to detect an object and electromagnetic waves.

In the following description, object sensors 291 equipped in the first to sixth holders 280-1 to 280-6 will be called first to sixth object sensors 291-1 to 291-6, and electromagnetic wave sensors 295 equipped in the first to sixth holders 280-1 to 280-6 will be called first to sixth electromagnetic wave sensors 295-1 to 295-6.

Figure 8:
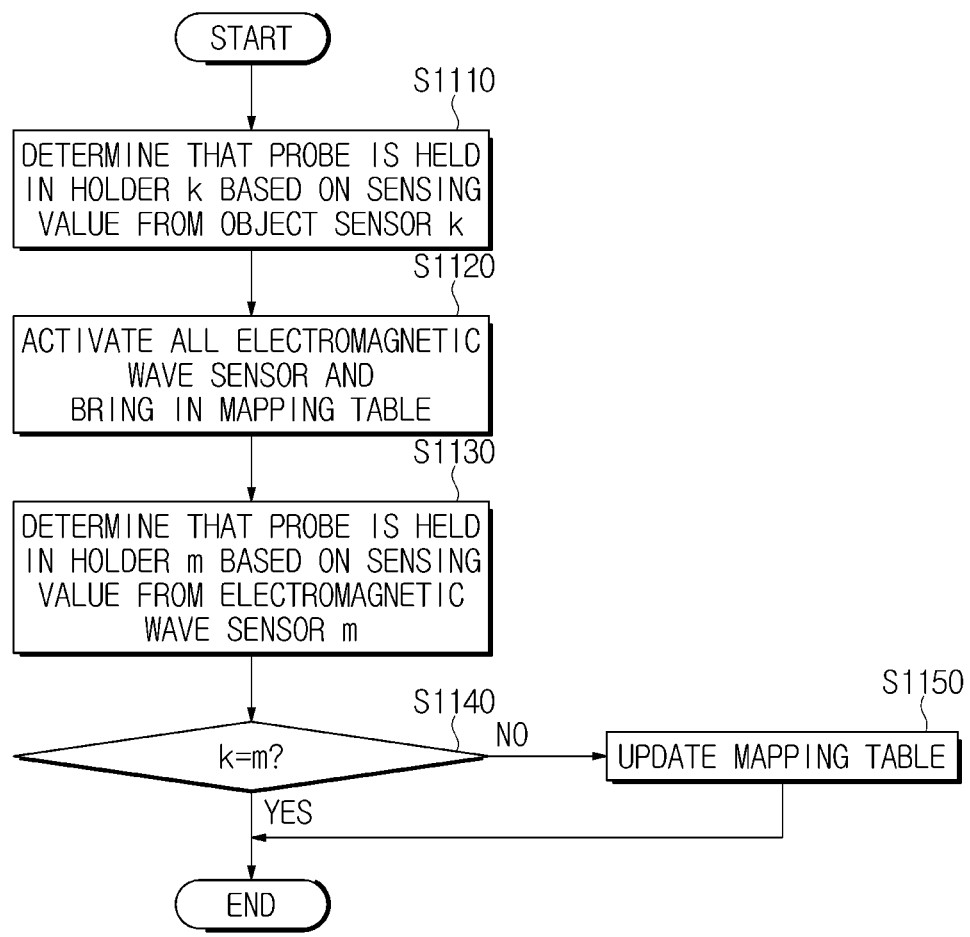
FIG. 8 is a flowchart illustrating a general method for controlling an ultrasound diagnostic apparatus with a probe held in a holder, according to an embodiment of the present disclosure.

FIG. 8 is a flowchart illustrating a general method for controlling an ultrasound diagnostic apparatus with a probe held in a holder, according to an embodiment of the present disclosure.

Reference numerals as will be cited in describing FIG. 8 are the same reference numerals as described in describing FIGS. 1 to 7C.

First, if the probe 100 is held in holder k while the first to sixth object sensors 291-1 to 291-6 equipped in the first to sixth holders 280-1 to 280-6 are activated, the object sensor sensing value processor 292 determines that the probe 100 is held in the holder k based on a sensing value from object sensor k, in operation S1110.

The controller 220 may determine whether the probe 100 held in is activated based on sensing values from the first to sixth electromagnetic wave sensors 295-1 to 295-6 arranged in the first to sixth holders 280-1 to 280-6, and may update the mapping table.

Specifically, the controller 220 determines that the probe 100 comes into contact with the object sensor k that corresponds to the holder k while the first to sixth object sensors 291-1 to 291-6 equipped in the first to sixth holders 280-1 to 280-6, respectively, are activated, i.e., the controller 220 determines that the probe 100 is now held in the holder k, in operation S1110. In this case, the probe may detect an operation status. The controller 220 then brings the stored existing mapping table with reference to sensing values from the first to sixth electromagnetic wave sensors 295-1 to 295-6, in operation S1120.

If electromagnetic wave sensor m detects activation of the probe 100, the electromagnetic wave sensor sensing value processor 296 may determine that a currently activated probe is held in holder m, based on the sensing value from the electromagnetic wave sensor m, in operation S1130.

Next, the controller 220 determines whether the holder k and the holder m correspond to each other, in operation S1140.

If the holder k and the holder m corresponds to each other, the controller 220 keeps the mapping table intact, but otherwise, if the holder k and the holder m do not corresponds to each other, the controller 220 updates the mapping table, in operation S1150.

Specifically, if the holder k and the holder m do not correspond, the controller 220 activates all the ports 210-1 to 210-4 in a predetermined order, e.g., in a sequential order, and the electromagnetic wave sensor sensing value processor 296 examines each of the holder 280-1 to 280-6 corresponding to one of the ports 210-1 to 210-4 based on sensing values collected from the first to sixth electromagnetic wave sensors 291-1 to 291-6. The controller 220 then newly updates the mapping table with a holder name corresponding to each port name.

For example, if the holder k and the holder m do not correspond, the controller 220 first activates the first port 210-1, activates the first to sixth electromagnetic wave sensors 291-1 to 291-6, and maps the second holder 280-2 and the first port 210-1 if an electromagnetic wave is detected by the second electromagnetic wave sensor 291-2 equipped in the second holder 280-2 when the probe 100 is held in the second holder 280-2.

Next, the controller 220 activates the second port 210-2, activates the first to sixth electromagnetic wave sensors 291-1 to 291-6, and maps the fourth holder 280-4 and the second port 210-2 if an electromagnetic wave is detected by the fourth electromagnetic wave sensor 291-4 equipped in the fourth holder 280-4 when the probe 100 is held in the fourth holder 280-4.

Subsequently, the controller 220 activates the third port 210-3, activates the first to sixth electromagnetic wave sensors 291-1 to 291-6, and maps the fifth holder 280-5 and the third port 210-3 if an electromagnetic wave is detected by the fifth electromagnetic wave sensor 291-5 equipped in the fifth holder 280-5 when the probe 100 is held in the fifth holder 280-5.

Subsequently, the controller 220 activates the fourth port 210-4, activates the first to sixth electromagnetic wave sensors 291-1 to 291-6, and maps the first holder 280-1 and the fourth port 210-4 if an electromagnetic wave is detected by the first electromagnetic wave sensor 291-1 equipped in the first holder 280-1 when the probe 100 is held in the first holder 280-1.

The updated mapping table or the port name of the probe 100 held in the holder m may be indicated for the user through the display unit 260.

Furthermore, if it is determined that the plurality of probes 100-1 to 100-6 are all held in any holders 280, operation of all the probes 100-1 to 100-6 may be automatically stopped (Auto Freeze).

While the previous embodiments show that the first to fourth ports 210-1 to 210-4 are mapped to the second, fourth, fifth, and first holders 280-2, 280-4, 280-5, and 280-1, respectively, the present disclosure is not limited thereto.

Figure 9:
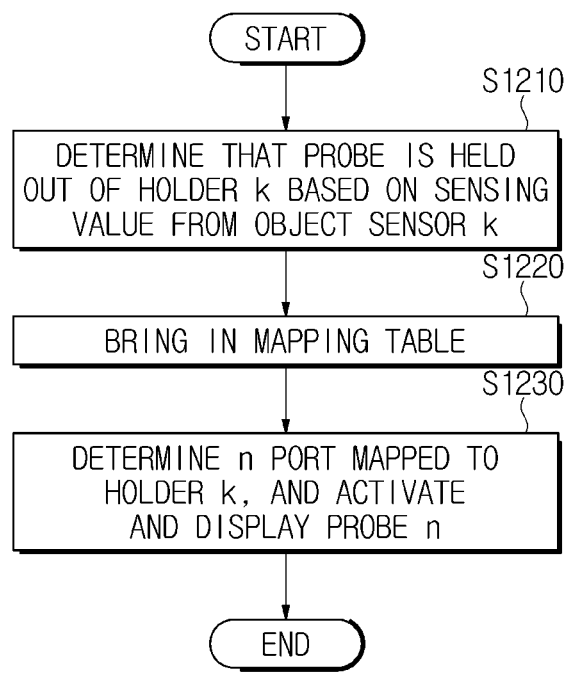
FIG. 9 is a flowchart illustrating a general method for controlling an ultrasound diagnostic apparatus with a probe held out of a holder, according to an embodiment of the present disclosure.

FIG. 9 is a flowchart illustrating a general method for controlling an ultrasound diagnostic apparatus with a probe held out of a holder, according to an embodiment of the present disclosure. Reference numerals as will be cited in describing FIG. 9 are the same reference numerals as described in describing FIGS. 1 to 7C.

First, if the probe 100 is held out of holder k while the first to sixth object sensors 291-1 to 291-6 equipped in the first to sixth holders 280-1 to 280-6 are activated, the object sensor sensing value processor 292 determines that the probe 100 is held out of the holder k based on a sensing value from object sensor k, in operation S1210.

Next, the controller 220 may determine port n mapped to the holder k based on the stored mapping table in operation S1220, and activate probe n connected to the port n in operation S1230.

Furthermore, the current mapping table, or the port number (n) and port name of the probe 100 held out of the holder k may be indicated for the user through the display unit 260. In this case, the user may check the port name and manually type in whether the probe n is activated or not, through the input unit 270.

While the previous embodiments show that the plurality of ports 210-1 to 210-6 and the plurality of holders 280-1 to 280-6 are equipped in the single main body 200, the holders 280-1 to 280-6 may be equipped in separate devices and connected to the main body 200 over a wired/wireless communication network.

Figure 10:
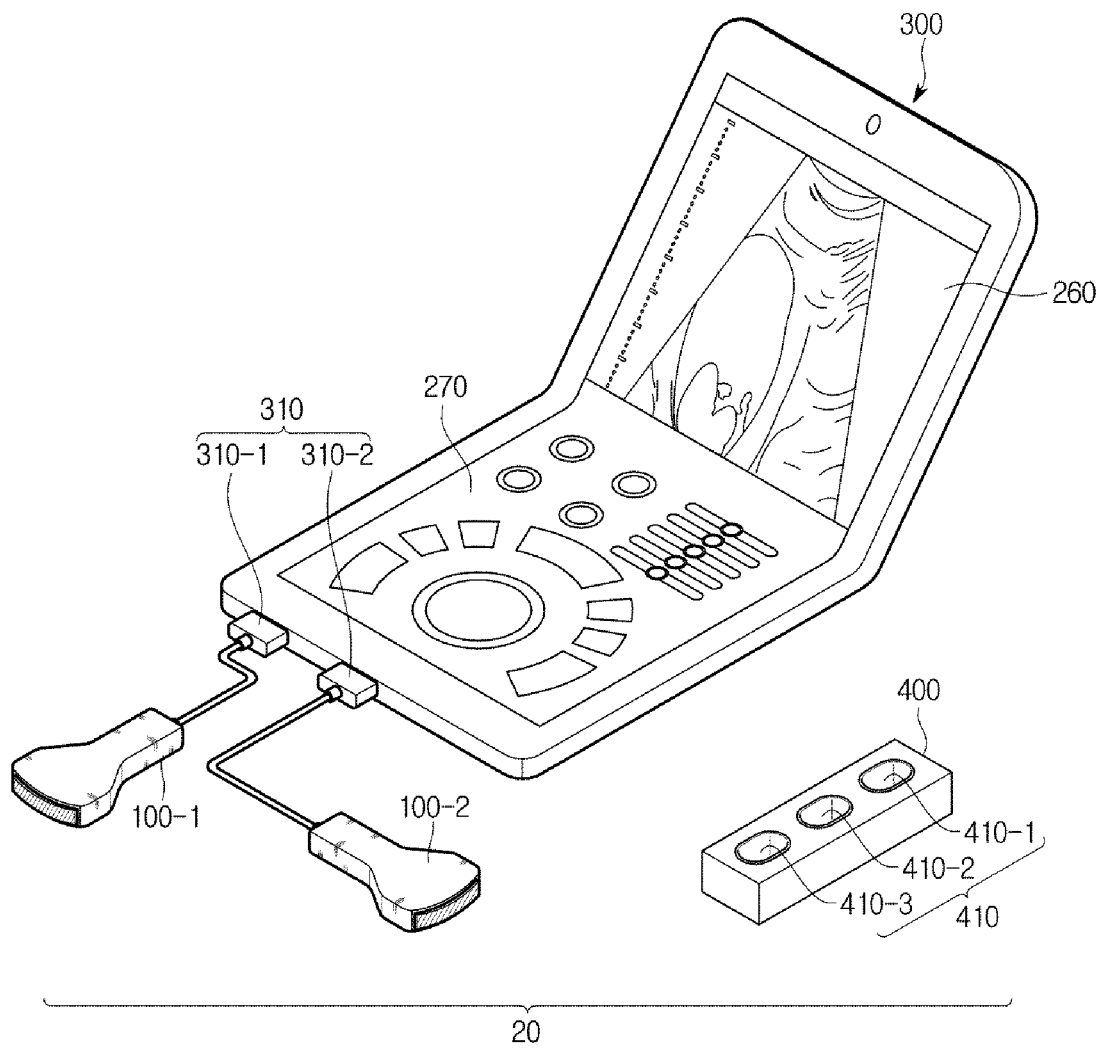
FIG. 10 is an exterior view of an ultrasound diagnostic apparatus, according to another embodiment of the present disclosure.
Figure 11:
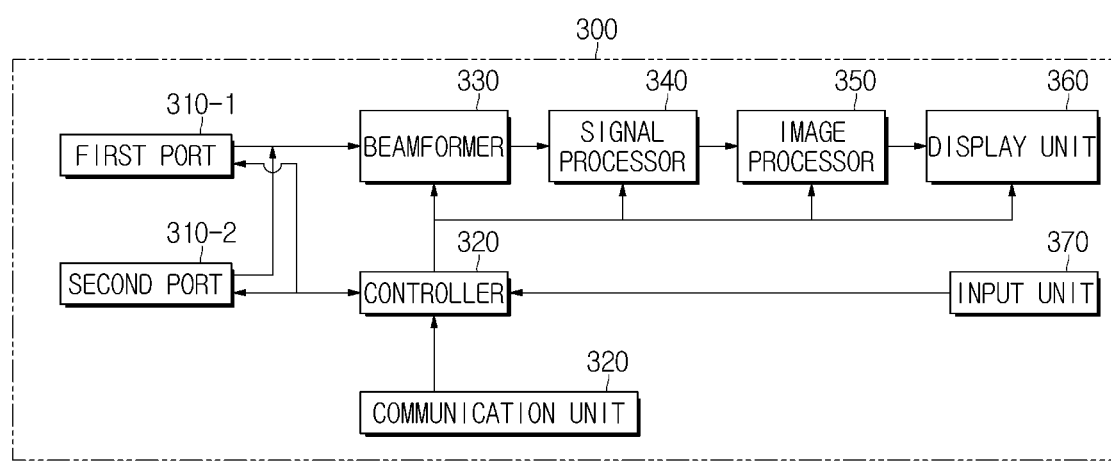
FIGS. 11 and 12 are control block diagrams of an ultrasound diagnostic apparatus, according to embodiments of the present disclosure.
Figure 12:
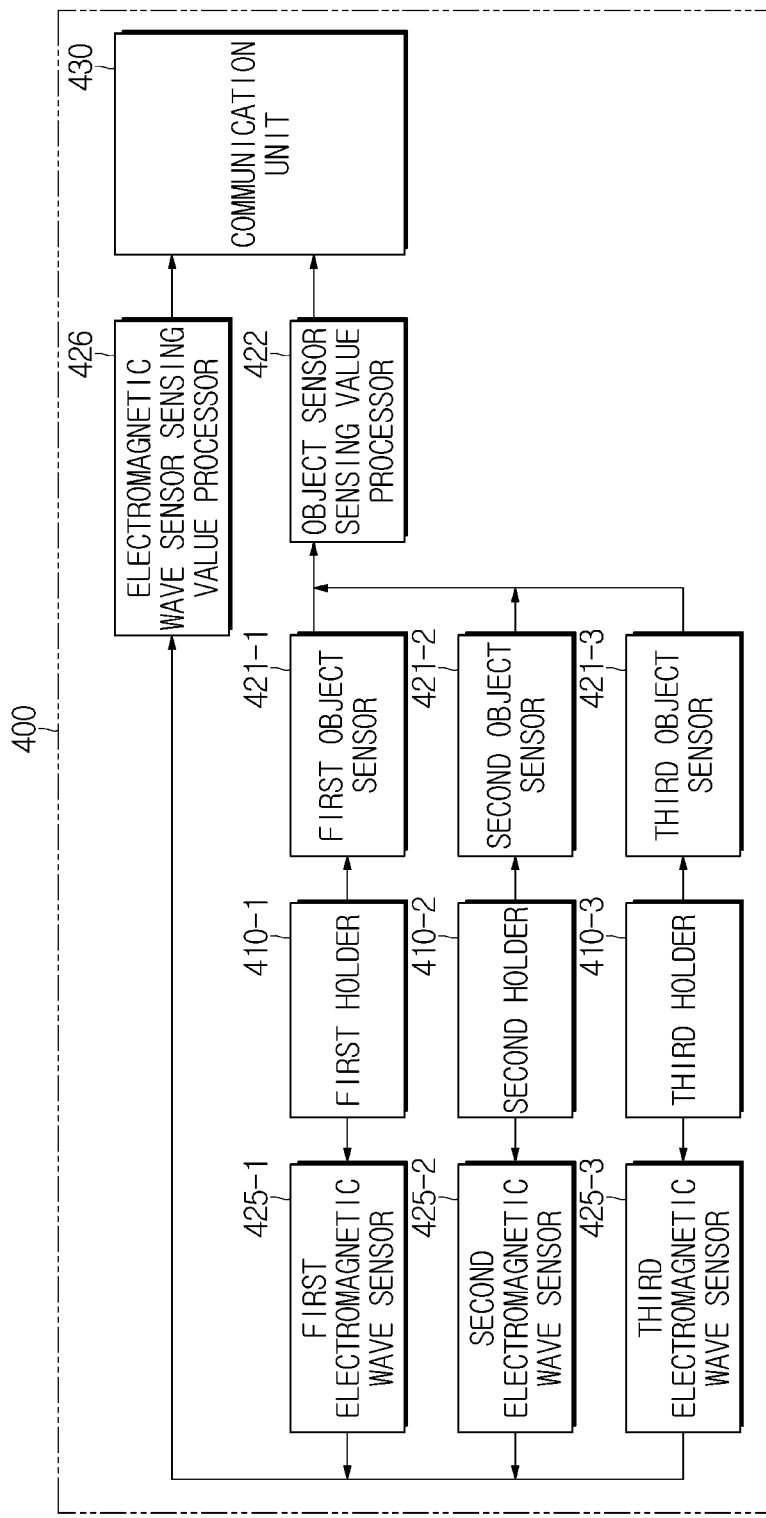

FIG. 10 is an exterior view of an ultrasound diagnostic apparatus, according to another embodiment of the present disclosure, and FIGS. 11 and 12 are control block diagrams of an ultrasound diagnostic apparatus, according to other embodiment of the present disclosure.

Referring to FIG. 10, an ultrasound diagnostic apparatus 20 in accordance with another embodiment of the present disclosure may include a main body 300 and a holder assembly 400. Although FIG. 10 shows that the main body 300 is implemented by a terminal or laptop having portability and mobility, the form of the main body 300 is not limited thereto.

The main body 300 may include at least one port 310 coupled with the probe 100, a display unit 360 for displaying various contents based on signals received from the probe 100, and an input unit 370 for receiving various commands from the user.

Similar to what is described above in connection with FIG. 1, the port 310 includes a plurality of ports 310-1 and 310-2, which may be coupled with first and second ports 310-1 and 310-2, respectively.

Functions of the port 310, display unit 360, and input unit 370 are the same as those of the port 210, display unit 260, and input unit 270 as described in connection with FIGS. 1 to 6, so the overlapping description will be omitted herein.

The holder assembly 400 may include a plurality of holders 410; 410-1 to 410-3 to hold the probe 100. The holder assembly 400 may be coupled with the main body 300 over a wired/wireless communication network. With the coupling between the main body 300 and the holder assembly 400, the main body 300 may receive sensing values from the holder assembly 400 and send control signals to the holder assembly 400.

For this, the main body 300 of FIG. 10 may include a controller 320, a beamformer 330, a signal processor 340, and an image processor 350 as in FIG. 6.

Functions of the controller 320, beamformer 330, signal processor 340, and image processor 350 are the same as those of the controller 220, beamformer 230, signal processor 240, and image processor 250 as described in connection with FIG. 6, so the overlapping description will be omitted herein.

The main body 300 may further include a communication unit 380, which may be connected to a communication unit 430 of a holder assembly 400 (see FIG. 12) over a wired/wireless communication network.

The communication unit 380 of the main body 300 may receive signals sent from the holder assembly 400 via the wired/wireless communication network. The signal sent from the holder assembly 400 may include e.g., information about a processing result of an object sensor sensing value processor 422 (see FIG. 12), and information about a processing result of an electromagnetic wave sensor sensing value processor 426 (see FIG. 12).

In this case, the controller 320 may update the mapping table based on the signal received from the holder assembly 400, or operate the probe 100 coupled with the port 310 by controlling at least one port 310.

The wired/wireless communication network may include a wired communication network, a wireless communication network, a short range communication network, and a combination of them.

The wired communication network may be connected via a USB or AUX cable, and may include a wired Ethernet, a Wide Area Network (WAN), a Value-Added Network (VAN), or the like.

A communication protocol of a wireless communication network may include an institute of electrical and electronics engineers' (IEEE's) WLAN standard, such as IEEE 802.11x.

The communication protocol may include code division multiple access (CDMA), frequency division multiple access (FDMA), time division multiple access (TDMA), orthogonal frequency division multiple access (OFDMA), single carrier frequency division multiple access (SC-FDMA), etc. The CDMA may be implemented in a radio technology, such as universal terrestrial radio access (UTRA) or CDMA2000. The TDMA may be implemented in a radio technology, such as global system for mobile communications (GSM), general packet radio service (GPRS), or enhanced data rates for GSM evolution (EDGE). The OFDMA may be implemented in a radio technology, such as IEEE 802.11 (Wi-Fi), IEEE 802.16 (WiMAX), IEEE 802-20, E-UTRA (evolved UTRA), etc. The IEEE 802.16m is an evolution of IEEE 802.16e, and provides backward compatibility with an IEEE 806.16e based system. The UTRA is a part of the universal mobile telecommunications system (UMTS). The 3rd generation partnership project (3GPP) long term evolution (LTE) is a part of the evolved UMTS (E-UMTS) that uses evolved-UMTS terrestrial radio access (E-UTRA), and employs OFDMA in downlink and SC-FDMA in uplink. LTE-Advanced (LTE-A) is an evolution of the 3GPP LTE.

Communication protocols of the short-range communication network may include bluetooth, bluetooth low energy, infrared data association (IrDA), Wi-Fi, Wi-Fi Direct, Ultra Wideband (UWB), Near Field Communication (NFC), Zigbee, etc.

Referring to FIG. 12, the holder assembly 400 in accordance with another embodiment of the present disclosure may include a plurality of holders 410-1 to 410-3, object sensors 421-1 to 421-3 and elecromagnetic wave sensors 425-1 to 425-3 equipped in the holders 410-1 to 410-3, an object sensor sensing value processor 422 for determining which one of holders 410-1 to 410-3 the probe 100 is held in or held out, based on sensing values collected from the plurality of object sensors 421-1 to 421-3, and an electromagnetic wave sensor sensing value processor 426 for determining which one of holders 410-1 to 410-3 the probe 100 is held in, based on sensing values collected from the plurality of electromagnetic wave sensors 425-1 to 425-3.

Functions of the holders 410-1 to 410-3, object sensors 421-1 to 421-3, electromagnetic wave sensors 425-1 to 425-3, object sensor sensing value processor 422, and electromagnetic wave sensor sensing value processor 426 are the same as those of the holders 210-1 to 210-3, object sensors 221-1 to 221-3, electromagnetic wave sensors 225-1 to 225-3, object sensor sensing value processor 222, and electromagnetic wave sensor sensing value processor 226, so the overlapping description will be omitted herein.

The holder assembly 400 may further include a communication unit 430, which may be connected to the communication unit 380 (see FIG. 11) of the main body 200 over a wired/wireless communication network.

The communication unit 430 of the holder assembly 400 may transmit signals to the main body 200 over the wired/wireless communication network. The signal sent from the holder assembly 400 may include e.g., information about a processing result of an object sensor sensing value processor 422, and information about a processing result of an electromagnetic wave sensor sensing value processor 426.

According to embodiments of the present disclosure of an ultrasound diagnostic apparatus, holder assembly, and method for controlling the ultrasound diagnostic apparatus, which port a probe held in a holder is coupled with may be recognized, and thus the user may freely use the probe without need to type in the port name.

Furthermore, according to embodiments of the present disclosure of an ultrasound diagnostic apparatus, holder assembly, and method for controlling the ultrasound diagnostic apparatus, the user may focus on the purpose of usage of the diagnostic apparatus without distraction in manipulation of the apparatus, e.g., without dispersion of gaze, and without requiring proficiency, and may thus appropriately determine a legion.

Several embodiments have been described, but a person of ordinary skill in the art will understand and appreciate that various modifications can be made without departing the scope of the present disclosure. Thus, it will be apparent to those ordinary skilled in the art that the true scope of technical protection is only defined by the following claims. For example, an element described in the singular form may be implemented as being distributed, and elements described in a distributed form may be implemented as being combined.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. An ultrasound diagnostic apparatus comprising:
a plurality of holders, each holder configured to hold a probe among a plurality of probes, each probe corresponding to a respective holder among the plurality of holders;
a plurality of ports, wherein each probe corresponds to a respective port of the plurality of ports;
a plurality of object sensors and a plurality of electromagnetic wave sensors, wherein each holder corresponds to a respective object sensor of the plurality of object sensors and a respective electromagnetic wave sensor of the plurality of electromagnetic wave sensors,
wherein each object sensor is configured to detect a status of whether the corresponding probe is held in the corresponding holder by sensing a conductor of the corresponding probe or detecting light from a light source of the corresponding holder;
wherein each electromagnetic wave sensor is configured to detect an operation status of the corresponding probe by sensing an electromagnetic wave radiated from the corresponding probe while being held in the corresponding holder; and
a controller configured to:
determine a first port, of the plurality of ports, corresponding to a first probe, of the plurality of probes, based on the status of the first probe and the operation status of the first probe,
determine that the first probe is held in a holder k of the plurality of holders based on a sensing value of an object sensor k of the plurality of object sensors that corresponds to said holder k, and subsequently determine that the first probe is held in a holder m of the plurality of holders based on a sensing value of an electromagnetic wave sensor m of the plurality of electromagnetic wave sensors that corresponds to said holder m,
determine whether said holder k corresponds with said holder m,
maintain a mapping table intact when said holder k and said holder m correspond to each other, and
update the mapping table when said holder k and said holder m do not correspond to each other.

2. The ultrasound diagnostic apparatus of claim 1, wherein each electromagnetic wave sensor comprises an Electro-Magnetic Interference (EMI) sensor arranged in or around the corresponding holder, and
wherein the EMI sensor is configured to detect a change in the electromagnetic wave radiated from the corresponding probe.

3. The ultrasound diagnostic apparatus of claim 1, wherein each object sensor comprises a photo interrupter arranged in or around the corresponding holder, and
wherein the photo interrupter comprises the light source for irradiating the light into the the corresponding holder and a light receiver for receiving the light.

4. The ultrasound diagnostic apparatus of claim 1, wherein the mapping table maps each port of the plurality of ports to a respective holder of the plurality of holders, and wherein the controller is further configured to update the mapping table by mapping the first port, which corresponds to the first probe, to said holder m.

5. The ultrasound diagnostic apparatus of claim 4, further comprising a sensing value processor for determining whether a probe n, of the plurality of probes is held in the holder k or held out of the holder k, based on the sensing value from the object sensor k.

6. The ultrasound diagnostic apparatus of claim 5, wherein the controller is further configured to determine a port name n, of the plurality of ports, that is mapped to holder k when the probe n is held out of the holder k, and activate the probe n that corresponds to the mapped port n when determining that the probe n is held out of holder k.

7. The ultrasound diagnostic apparatus of claim 5, further comprising a display device,
wherein the controller is further configured to determine a port n of the plurality of ports, that is mapped to the holder k when the probe n is held out of the holder k, and determine a holder name of the holder k and a port name of the mapped port n, and
wherein the display device is configured to display the holder name and the mapped port name.

8. The ultrasound diagnostic apparatus of claim 1, wherein the plurality of object sensors consists of a number of object sensors; the plurality of electromagnetic wave sensors consists of a number of electromagnetic wave sensors equal to the number of object sensors; and of the plurality of holders consists of a number of holders equal to the number of object sensors and the number of electromagnetic wave sensors.

9. The ultrasound diagnostic apparatus of claim 1, wherein the controller is further configured to stop operation of each respective probe of the plurality of probes when the respective probe is held in each holder of the plurality of holders.

10. A holder assembly comprising:
a plurality of holders, each holder configured to hold a probe among a plurality of probes, each probe corresponding to a respective holder among the plurality of holders;
a plurality of ports, wherein each probe corresponds a respective port of the plurality of ports;
a plurality of object sensors and a plurality of electromagnetic wave sensors, wherein each holder corresponds to a respective object sensor of the plurality of object sensors and a respective electromagnetic wave sensor of the plurality of electromagnetic wave sensors,
wherein each object sensor is configured to detect a status of whether the corresponding probe is held in the corresponding holder by sensing a conductor of the corresponding probe or detecting light from a light source of the corresponding holder;
wherein each electromagnetic wave sensor is configured to detect an operation status of the corresponding probe by sensing an electromagnetic wave radiated from the corresponding probe while being held in the corresponding holder;
a sensing value processor configured to:
determine whether a probe n, of the plurality of probes is held in a holder k, of the plurality of holders, or held out of the holder k based on a sensing value of an object sensor k of the plurality of object sensors and subsequently determine whether the probe n is held in a holder m, of the plurality of holders, or held out of the holder m based on a sensing value of an electromagnetic wave sensor m of the plurality of electromagnetic wave sensors, determine a port of the probe n based on the sensing value of the object sensor k and the sensing value of the electromagnetic wave sensor m; and a controller configured to:
determine whether the holder k corresponds with the holder m when the sensing value processor determines that the probe n is held in holder k based on the sensing value of the object sensor k and subsequently that the probe n is held in holder m based on the sensing value of the electromagnetic wave sensor m,
keep a mapping table intact when the holder k and the holder m correspond to each other,
update the mapping table when the holder k and the holder m do not correspond to each other.

11. The holder assembly of claim 10, further comprising a communication device configured to send a result of the determination of the sensing value processor to a main body of an ultrasound diagnostic apparatus.

12. The holder assembly of claim 10, wherein each electromagnetic wave sensor comprises an Electro-Magnetic Interference (EMI) sensor arranged in or around the corresponding holder, and
wherein the EMI sensor is configured to detect a change in the electromagnetic wave radiated from the corresponding probe.

13. The holder assembly of claim 10, wherein each object sensor comprises a photo interrupter arranged in or around the corresponding holder, and
wherein the photo interrupter comprises the light source of the corresponding holder, wherein the light source is for irradiating the light into the corresponding holder, and wherein the photo interrupter further comprises a light receiver for receiving the light.

14. A method for controlling an ultrasound diagnostic apparatus, the method comprising steps of:
detecting, by an object sensor k of a plurality of object sensors, a status of whether a probe n, of a plurality of probes, is held in a holder k of a plurality of holders, each probe of the plurality of probes corresponding to a respective holder among the plurality of holders, wherein each probe corresponds to a respective port of a plurality of ports, and wherein each holder corresponds to a respective object sensor of the plurality of object sensors;
subsequently detecting, by an electromagnetic wave sensor m of a plurality of electromagnetic wave sensors, an operation status of the probe n by sensing an electromagnetic wave radiated from the probe n while being held in a holder m of the plurality of holder, wherein each holder corresponds to a respective electromagnetic wave sensor of the plurality of electromagnetic wave sensors; and
determining, by a controller, a port name of the probe n based on the status of the probe n and a sensing value of the electromagnetic wave sensor m,
wherein the step of determining a port name of the probe n includes:
determining that the probe n is held in holder k based on a sensing value of the object sensor k,
subsequently determining that the probe n is held in holder m based on the sensing value of the electromagnetic sensor m, and
determining that the holder k corresponds with the holder m,
wherein, when the holder k and the holder m correspond to each other, the controller keeps a mapping table intact,
wherein, when the holder k and the holder m do not correspond to each other, the controller updates the mapping table.

15. The method of claim 14, further comprising a step of activating, by the controller, the probe n based on the mapping table, when it is determined that the probe n is held out of a holder, of the plurality of holders, that corresponds to the probe n.

* * * * *

UNITED STATES PATENT AND TRADEMARK OFFICE
CERTIFICATE OF CORRECTION

PATENT NO. : 10,973,493 B2  
APPLICATION NO. : 15/094409  
DATED : April 13, 2021  
INVENTOR(S) : Chil Su Kim Page 1 of 1

It is certified that error appears in the above-identified patent and that said Letters Patent is hereby corrected as shown below:

In the Claims

Column 13
Lines 56 through 61:
"3. The ultrasound diagnostic apparatus of claim 1, wherein the object sensor comprises a photo interrupter arranged in or around the corresponding holder, and wherein the photo interrupter comprises a light source for irradiating light into the the corresponding holder and a light receiver for receiving the light."

Should read:
--3. The ultrasound diagnostic apparatus of claim 1, wherein the object sensor comprises a photo interrupter arranged in or around the corresponding holder, and wherein the photo interrupter comprises a light source for irradiating light into the corresponding holder and a light receiver for receiving the light.--

Signed and Sealed this  
Fourth Day of February, 2025

Coke Morgan Stewart  
*Acting Director of the United States Patent and Trademark Office*